United States Patent [19]

Croxson

[11] Patent Number: 5,108,891
[45] Date of Patent: Apr. 28, 1992

[54] AIDS ASSAY

[75] Inventor: Thomas S. Croxson, Tenafly, N.J.

[73] Assignee: Beth Israel Medical Center, New York, N.Y.

[21] Appl. No.: 204,568

[22] Filed: Jun. 9, 1988

[51] Int. Cl.$^5$ .......................................... G01N 33/569
[52] U.S. Cl. .................................. 435/5; 435/7.9; 435/7.92; 435/974; 436/5.8; 436/531; 436/825; 436/826
[58] Field of Search ................ 435/5, 7, 21, 974; 436/518, 531, 825, 826

[56] References Cited

U.S. PATENT DOCUMENTS

| | | | |
|---|---|---|---|
| 4,166,104 | 8/1979 | Wagner et al. | 436/505 |
| 4,238,471 | 12/1980 | Reese et al. | 436/527 |
| 4,520,113 | 5/1985 | Gallo et al. | 435/5 |
| 4,600,690 | 7/1986 | Karmen et al. | 436/517 |
| 4,666,866 | 5/1987 | Krauth | 436/518 |
| 4,748,110 | 5/1988 | Paul | 435/5 |
| 4,786,591 | 11/1988 | Draeger et al. | 435/7 |
| 4,870,003 | 9/1989 | Kortright et al. | 435/5 |
| 4,886,742 | 12/1989 | Kortright et al. | |

OTHER PUBLICATIONS

Croxson et al., "HIV p24 Binding Capacity of Whole Salivarin HIV Seropositive People", J. Dental Res. 68(1989) 190.
Cowan, et al., Journal of Clinical Microbiology, vol. 26, No. 11, Nov. 1988, pp. 2421–2422.
Allain, et al., The New England Journal of Medicine, vol. 317, No. 18, Oct. 29, 1987, pp. 1114–1121.
Biggar et al., British Medical Journal, vol. 291, Oct. 12, 1985, pp. 997–998.
Forster et al., AIDS, 1987, vol. 1, No. 4, pp. 235–240.
Goudsmit, et al., The Journal of Infectious Diseases, vol. 155, No. 3, Mar. 1987, pp. 558–560.
Groopman, et al., Journal of Infectious Diseases, vol. 153, No. 4, Apr. 1986, pp. 736–742.
Kwok et al., J. Virol., 1987, vol. 61, pp. 1690–94.
Lange et al., British Medical Journal, vol. 292, Jan. 25, 1986, pp. 228–230.
McDougal, et al., J. Immunol. Methods, 1985, vol. 76, pp. 171–183.
Moss et al., Br. Med. J., 1988, vol. 296, pp. 745–750.
Pan et al., Journal of Infectious Diseases, vol. 155, No. 4, Apr. 1987, pp. 626–632.
Pedersen, et al., British Medical Journal, vol. 295, 1987, pp. 567–569.
Spira, et al., The New England Journal of Medicine, vol. 317, No. 17, Oct. 22, 1987, pp. 1093–1094.
Ujhelyi et al., AIDS, 1987, vol. 1, pp. 161–165.
Weber et al., Lancet, Jan. 17, 1987, pp. 119–122.

(List continued on next page.)

Primary Examiner—Christine Nucker

[57] ABSTRACT

An assay which is responsive to the levels of anti-p24 antibodies in serum samples is provided which comprises the steps of: (a) forming a test mixture comprising the sample and an antigen solution containing free p24 antigen within a predetermined concentration range: (b) incubating the test mixture under conditions whereby anti-p24 antibodies from the sample, if any, can react with the free p24 antigen to form antibody-antigen complexes; (c) determining the concentration of free p24 antigen remaining in the test mixture after the incubation; (d) determining the concentration of free p24 antigen in the antigen solution; and (e) calculating the difference between the concentration of free p24 antigen in the antigen solution and the concentration of freee p24 antigen in the test mixture after the incubation.

The difference calculated in step (e) represents the "binding capacity" of the serum sample for p24 antigen. This parameter is shown to serve as an accurate and convenient measure of a patient's level of anti-p24 antibodies. In certain preferred embodiments, the anti-p24 antibody assay is integrated with a p24 antigen assay so that declining anti-p24 antibody levels in combination with rising p24 antigen levels can be readily monitored. This combination has been found to generally indicate a poor prognosis for HIV-infected patients.

10 Claims, 9 Drawing Sheets

OTHER PUBLICATIONS

Wolf, et al., *British Medical Journal*, vol. 295, 1987, pp. 569-572.

Yarchoan et al., *New England J. Med.*, 1987, vol. 316, pp. 557-564.

"Classification System for Human T-Lymphotropic Virus Type III/Lymphadenopathy-Associated Virus Infections", *MMWR*, May 23, 1986, pp. 334-339.

Abstract presented at the Twelfth International Apheresis Symposium, Washington DC, Apr. 27-29, 1987. (Huskens et al.,).

Abstract presented at the UCLA Symposia on Molecular and Cellular Biology, Mar. 29-May 1, 1987. (Reagan et al.).

Goudsmit et al., *Lancet*, Jul. 26, 1986, pp. 177-180.

Allain et al., *Lancet*, Nov. 29, 1986, pp. 1233-1236.

AIDS ASSAY

BACKGROUND OF THE INVENTION

This invention relates to the acquired immune deficiency syndrome (AIDS) and, in particular, to assays which function as prognostic indicators of the development of AIDS by people infected with the human immunodeficiency virus (HIV).

The human immunodeficiency virus has been established as the etiologic agent of AIDS, chronically infecting and eventually killing cells critical to normal immunologic function. In addition to producing end-stage AIDS, HIV directly or indirectly contributes to immunologic dysfunction characterized clinically by the development of persistent generalized lymphadenopathy and AIDS-related complex (ARC). HIV-infected patients are usually staged by clinical findings and the numbers of CD4 positive lymphocytes (helper cells).

Patients infected with HIV can remain essentially symptom free for years, e.g., three years or longer, and not all HIV-infected people actually progress to AIDS. See, for example, Weber et al., "Human immunodeficiency virus infection in two cohorts of homosexual men: neutralizing sera and association of anti-gag antibody with prognosis," Lancet, Jan. 17, 1987, pages 119-121. As a result, extensive efforts have been made to develop laboratory tests which are prognostic indicators of the development of AIDS, ARC and other AIDS-related conditions by persons infected with HIV. See, for example, Spira, et al., "Human Immunodeficiency Virus Viremia as a Prognostic Indicator in Homosexual Men with Lymphadenopathy Syndrome," The New England Journal of Medicine, Vol. 317, No. 17, Oct. 22, 1987, pages 1093-1094. The need for predictive tests has become increasingly important as anti-HIV therapies directed at suppressing HIV replication have been developed. See, for example, Forster et al., "Decline of Anti-p24 Antibody Precedes Antigenaemia as Correlate of Prognosis in HIV-1 Infection," AIDS, 1987, Vol. 1, No. 4, pages 235-240.

One indicator which has been considered is the level of p24 antigen in a patient's serum, i.e., p24 antigenemia. See, for example, Wolf, et al., "Risk of AIDS Related Complex and AIDS in Homosexual Men with Persistent HIV Antigenaemia," British Medical Journal, Vol. 295, 1987, pages 569-572. In particular, an increase in the level of p24 antigen has been associated with progression to AIDS. Thus, Forster et al., supra, report that in 40% of the AIDS patients in their study, detectable levels of p24 antigen were seen 2 years prior to the actual development of AIDS.

The level of anti-p24 antibodies in a patient's serum has also been considered for use as a prognostic indicator. In this case, a decrease in the level of anti-p24 antibodies has been associated with progression to AIDS. See Biggar, et. al., "Variation in Human T Lymphotropic Virus III (HTLV-III) Antibodies in Homosexual Men: Decline Before Onset of Illness Related to Acquired Immune Deficiency Syndrome (AIDS)," British Medical Journal, Volume 291, Oct. 12, 1985, pages 997-998; Lange, et al., "Distinct IgG Recognition Patterns During Progression of Subclinical and Clinical Infection with Lymphadenopathy Associated Virus/-Human T Lymphotropic Virus," British Medical Journal, Vol. 292, Jan. 25, 1986, pages 228-230; Pan et. al., "Patterns of Antibody Response in Individuals Infected with the Human Immunodeficiency Virus," Journal of Infectious Diseases, Vol. 155, No. 4, Apr. 1987, pages 626-632: Weber, et al., supra. As reported by Forster et al., supra, this indicator can provide predictive information up to 18 months earlier than the antigenemia indicator. (Note that Groopman, et al., "Serological Characterization of HTLV-III Infection in AIDS and Related Disorders," Journal of Infectious Diseases, Vol. 153, No. 4, Apr. 1986, pages 736-742, have found anti-p24 antibodies in both symptomatic and asymptomatic seropositive individuals.)

A number of recent studies have concluded that the combination of an increasing p24 antigen level and a declining anti-p24 antibody level is predictive of HIV-related clinical complications, including AIDS. See Allain, et al., "Long-Term Evaluation of HIV Antigen and Antibodies to p24 and gp41 in Patients with Hemophilia," The New England Journal of Medicine, Vol. 317, No. 18, Oct. 29, 1987, pages 1114-1121: Forster, et al., supra: Goudsmit, et al., "Antigenemia and Antibody Titers to Core and Envelope Antigens in AIDS, AIDS-Related Complex, and Subclinical Human Immunodeficiency Virus Infection," The Journal of Infectious Diseases, Vol. 155, No. 3, Mar. 1987, pages 558-560; Pedersen, et al., "Temporal Relation of Antigenaemia and Loss of Antibodies to Core Antigens to Development of Clinical Disease in HIV Infection," Britisn Medical Journal, Vol. 295, 1987, pages 567-569.

Various highly-sensitive assays for p24 antigen levels have been developed and are available from such companies as Abbott Laboratories (North Chicago, Ill.) and E. I. Du Pont de Nemours & Co. (Biomedical Products Department, Boston, Mass.). See, for example, Allain et al., supra: Forster, et al., supra; Goudsmit, et al., supra; Wolf, et al., supra. These assays employ a sandwich assay format in which serum samples are incubated with bound and enzyme-labelled anti-p24 antibodies to form an antibody/p24-antigen/antibody sandwich. Concentrations of p24 antigen are determined from standard curves obtained by performing the assay on a series of standards containing known amounts of p24 antigen. With these assays, p24 antigen levels on the order of 50 picograms/milliliter can be detected. See also Pedersen, et al., supra.

Assays for anti-p24 antibodies have also been developed. These assays suffer from a number of problems. The early assays, which continue to be used, employed Western blot techniques in which HIV virus proteins were separated by SDS-PAGE, transferred to a nitrocellulose sheet, incubated with the test serum, and developed using an antihuman IgG from an appropriate animal and a suitable enzyme-labeling system. See Biggar, et al., supra: Lange, et al., supra: Groopman, et al., supra: Pan, et al., supra. These assays were obviously difficult to perform, time consuming, and not well-suited for use in a clinical laboratory setting. See Pan, et al., supra. Also, the assays did not give reliable quantitative measures of anti-p24 antibodies in sera being tested. Radioimmunoprecipitation assays (RIPA) using radiolabeled antigens, immobilized test sera, and SDS-PAGE separation, have also been employed. See, for example, Weber, et al., supra. These assays suffer from the same problems as the Western blot assays and are not suitable for wide spread clinical use.

More recently, enzyme immunoassays for anti-p24 antibodies have been developed. See, for example, Forster, et al., supra. In particular, Abbott Laboratories has developed an assay in which beads coated with recombinant HIV core antigen, including p24 antigen, are incubated with serial dilutions of the serum being analyzed and with enzyme-labelled antibody to HIV core antigen. After a 16–22 hour incubation, the beads are washed and developed using a suitable substrate for the enzyme label. Since this is a competitive assay, the amount of antibody in the sample is inversely related to the intensity of the color generated during the development step. Positive and negative controls are run to establish a cutoff level for the presence of anti-p24 antibody, i.e., the midpoint between the controls. Titers are defined as the highest dilution which produces a color level below the cutoff. See Goudsmit, et al., supra; Pedersen, et al., supra. A similar competitive assay has been described by Weber, et al., supra. Significantly, Weber, et al., found that the classical radioimmunoprecipitation procedure was more sensitive than the competitive assay procedure. In addition to these competitive assays, direct ELISA assays for anti-p24 antibodies employing immobilized antigen and enzyme-labelled anti-human globulin antibodies have also been considered.

The primary disadvantage of these assay systems is that they employ serial dilutions of the patient's serum. Accordingly, in essence, numerous individual assays and measurements must be made to arrive at an antibody titer. This makes the assays difficult to use, labor intensive, and expensive. Indeed, Pedersen, et al., supra, after specifically pointing out that prognostic tests must be simple to do and interpret, recommended using a p24 antigen test for selecting patients for antiviral treatment, but significantly did not recommend using the Abbott competitive enzyme immunoassay for anti-p24 antibodies for this purpose.

Recently, a variation of the Abbott assay has been reported by Allain, et al., supra, in which titers are calculated by comparison with a reference curve obtained by serial dilutions of a sample containing standard antibody. The range of titers which can be measured by the modified assay is only between 1:2 and 1:256, and the assay requires the determination of a cutoff point for each series of assays so that the recorded optical densities can be transformed to titers using the standard curve.

Significantly, with regard to the enzyme immunoassays for anti-p24 antibodies, as well as all of the other assays for these antibodies, there is no integration between the assay for antibody levels and an assay for p24 antigen levels. As discussed above, it is the combination of a falling antibody level and a rising antigen level which appears to be most predictive of the clinical course of an HIV infection. Yet, as presently practiced, completely separate assays are being performed for these two important prognostic indicators.

SUMMARY OF THE INVENTION

In view of the foregoing state of the art, it is an object of this invention to provide an assay which is responsive to the levels of anti-p24 antibodies in a biological fluid, e.g., a serum sample, and which is easier to perform, less expensive, and more suitable for wide spread clinical use than existing anti-p24 antibody assays. It is a further object of this invention to provide an assay for anti-p24 antibodies which can be readily integrated with a p24 antigen assay so that both assays can be conveniently performed simultaneously. In this way, the combination of a falling level of anti-p24 antibodies and a rising level of p24 antigen can be readily detected. As discussed above, this combination has been found to be indicative of a poor prognosis for HIV-infected patients.

To achieve the foregoing and other objects, the invention, in accordance with certain of its aspects, provides an assay which is responsive to the levels of anti-p24 antibodies in a sample of a biological fluid comprising the steps of:

(a) forming a test mixture comprising: 1) the sample; and 2) a solution (hereinafter referred to as the "p24 antigen solution" or simply the "antigen solution") containing free p24 antigen within a predetermined concentration range, the relative amounts of the sample and the antigen solution being such that the concentration of free p24 antigen in the antigen solution is not substantially diluted by the formation of the test mixture;

(b) incubating the test mixture under conditions whereby anti-p24 antibodies from the sample, if any, can react with the free p24 antigen to form antibody-antigen complexes;

(c) determining the concentration of free p24 antigen remaining in the test mixture after the incubation;

(d) determining the concentration of free p24 antigen in the antigen solution; and (e) calculating the difference between the concentration of free p24 antigen in the antigen solution and the concentration of free p24 antigen in the test mixture after the incubation.

The difference calculated in step (e) is referred to herein as the sample's "p24 binding capacity" or simply the sample's "binding capacity". This parameter has been found to be an accurate and convenient measure of the level of anti-p24 antibodies in patient samples.

Specifically, the higher the level of anti-p24 antibodies in a sample, the more antibody-antigen complexes which are formed in step (b); the more antibody-antigen complexes which are formed in step (b), the lower the concentration of free p24 antigen determined in step (c); the lower the concentration of free p24 antigen determined in step (c), the larger the binding capacity value calculated in step (e). Accordingly, the higher the level of anti-p24 antibodies, the larger the calculated binding capacity. This straightforward relation between binding capacity and the level of anti-p24 antibodies is easily understood by both patient and physician, which is an important advantage of the assay.

Another important advantage of the assay is that it can be readily integrated with existing assays for p24 antigen levels. Specifically, in accordance with this further aspect of the invention, an assay system responsive to both anti-p24 antibody levels and p24 antigen levels is provided which comprises the steps of:

(a) forming the test mixture of the anti-p24 antibody assay using 1) a first sample from the biological fluid to be tested, and 2) the p24 antigen solution;

(b) incubating the test mixture;

(c) assaying the test mixture for p24 antigen concentration; and (d) assaying a second sample from the biological fluid for p24 antigen concentration;

the assays of step (c) (for the level of anti-p24 antibodies) and step (d) (for the level of p24 antigen) being performed substantially simultaneously using the same assay technique.

This assay system is readily incorporated in a clinical laboratory setting. Indeed, the assay for the level of anti-p24 antibodies in essence boils down to simply running the p24 antigen assay on additional samples, i.e., samples which have been mixed with the antigen solution. Accordingly, the integration of the anti-p24 antibody assay with the p24 antigen assay involves a minimum of additional steps and new procedures. This straightforward integration is in direct contrast to the existing anti-p24 antibody assays discussed above which essentially have no commonality with p24 antigen assays.

In certain preferred embodiments of the invention, p24 antigen levels are measured by a sandwich assay technique using anti-p24 antibodies, e.g., a bound (immobilized) anti-p24 antibody and a soluble anti-p24 antibody which carries a label or is labelled as part of the assay procedure. In other preferred embodiments, the same assay procedure used to measure p24 antigen levels in the test mixture (and in the second sample when the assay system is employed) is used to determine the concentration of p24 antigen in the antigen solution. This concentration can be determined at the same time the p24 antigen level in the test mixture is determined or can be determined separately either before or after the test mixture is assayed. In a clinical laboratory setting, the p24 antigen level in the antigen solution will generally be, and preferably is, determined at the same time the p24 antigen level in the test mixture is determined both as a control for the assay and so as to minimize assay-to-assay variations in the calculated binding capacity.

The description of the preferred embodiments set forth below further describes the principles and advantages of the present invention.

DESCRIPTION OF THE PREFERRED EMBODIMENTS

As discussed above, the present invention relates to 1) an assay which is responsive to the level of anti-p24 antibodies in a biological fluid, and 2) the integration of that assay with p24 antigen assays.

The biological fluid to be tested will usually be human serum. Other biological fluids which can be tested include whole blood, plasma, cerebrospinal fluid (CSF), saliva, and the like. Although to date there has been only limited success in developing animal and laboratory models for use in studying AIDS, the present invention can be used in testing biological fluids from the models which presently exist as well as those that may be developed in the future.

The assay can be performed on both diluted and undiluted samples of the biological fluid. In the case of human serum, undiluted samples are preferred. If dilution is desired, a suitable dilution medium comprises phosphate buffered saline containing 0.5% or 1% normal human sera. When diluted samples are used, the binding capacity for the biological fluid is calculated by multiplying the binding capacity calculated for the diluted sample by the dilution factor, e.g., by 2 in the case of a sample which has been diluted by 1:2.

To perform the assay, the sample of the biological fluid is mixed with a measured quantity of a p24 antigen solution which contains p24 antigen within a predetermined concentration range. The p24 antigen can be obtained in various ways including the lysis of whole virus grown in culture and through the use of recombinant DNA techniques. p24 antigen from viral lysates has been found preferable for use with the invention because of the low solubility in physiological saline of existing recombinant p24 proteins. The entire p24 molecule need not be used, but rather only those parts of the molecule which will bind to anti-p24 antibodies in patient samples and which can be detected by p24 antigen assays.

A viral lysate was used in the examples presented below. This lysate was prepared from an HIV isolate (HIV$_{hs}$) recovered from a homosexual patient with Kaposi's sarcoma (KS) as follows. HIV$_{hs}$ was passaged twice (P2) in normal PHA-stimulated peripheral blood lymphocytes cultured in RPMI 1640 media (M.A. Bioproducts/Whittacker) with 20% fetal calf serum (Whittacker) and 10% T cell growth factor (Electro Nucleonics, Inc). The cell culture supernatant was clarified by centrifugation at 600×g for 20 minutes (twice), diluted in phosphate buffered saline with 0.5% (v/v) Triton X-100 (Sigma), and stored in aliquots at −70° C. until used. Just prior to use, normal human serum was added at a concentration of 0.5%. The final p24 antigen concentration in the antigen solution was between 350 ng/l (nanograms/liter) and 450 ng/l.

The concentration of p24 antigen in the antigen solution as well as the relative amounts of sample and antigen solution used in performing the assay are critical to the assay's success. Specifically, these quantities must be selected so that the assay is responsive to the levels of anti-p24 antibodies which exist at difference stages of HIV infection. The quantities must also be chosen to take account of the variability in anti-p24 antibody levels among patients at the same stage of infection.

In practice, the quantities are determined by testing a bank of sera samples taken from various patients through the course of their infection. Using this technique for the viral lysate described above and for the assay protocol described below, it was determined that: 1) the concentration of p24 antigen in the antigen solution should be between about 350 ng/l and about 450 ng/l, and preferably between about 380 ng/l and about 425 ng/l, where the antigen concentrations are measured using the Du Pont p24 assay described below; and 2) the antigen solution to sample ratio for undiluted sera should be approximately 250 parts solution to 1 part sample (in particular, in the examples presented below, 250 mcl (microliters) of antigen solution were combined with 1 mcl of sample). As will be evident to persons of ordinary skill in the art, the same technique can be used to determine the corresponding concentrations and solution/sample ratios for other assay protocols, sera dilutions, antigen sources and p24 assay systems.

In performing the assay, the sample to be tested and the antigen solution are mixed together to form a test mixture, and the test mixture is incubated under conditions whereby anti-p24 antibodies from the sample can react with free p24 antigen in the antigen solution. Various incubation times and temperatures can be used. For example, in the examples presented below, the antigen solution and the samples were incubated for 30 minutes at 37° C. in a shaking water bath. Essentially identical results were achieved with an incubation period of a few minutes at 37° C.

At least some further reaction between the free p24 antigen from the antigen solution and the anti-p24 antibodies from the sample takes place during the incubation portion of the p24 antigen assay, e.g., for a forward sandwich assay during the incubation of the sample with the immobilized antibody. If desired, the assay of the present invention can be formatted without a separate incubation of the test mixture prior to the commencement of the p24 antigen assay, the incubation portion of the p24 antigen assay serving as the incubation step of the present assay for this format. Formats of this kind wherein the incubation portion of the p24 antigen assay is conducted at a temperature below 37° C., e.g., at room temperature, will in general produce somewhat different values for p24 binding capacity than formats which include a separate incubation step at 37° C.

After the sample and the antigen solution have been combined and the p24 antigen/anti-p24 antibody complexes have formed, the concentration of free p24 antigen remaining in the test mixture is determined. This concentration can be determined by a variety of methods now known or subsequently developed. For example, as discussed above, commercial sandwich assays having sensitivities on the order of 50 picograms/milliliter (pg/ml) are available from Abbott and Du Pont. In particular, the Du Pont assay discussed below has a low limit of 31 pg/ml. These as well as other assays can be used in the practice of the invention.

The examples presented below used an antigen capture enzyme immunoassay sold by Biotechnology Systems, E. I. Du Pont, Billerica, Mass. (hereinafter referred to as the "Du Pont assay"). See McDougal, et al., "Immunoassay for the detection and quantitation of infectious human retrovirus, lymphadenopathy-associated virus (LAV)", *J. Immunol. Methods,* 1985, Vol. 76, pages 171–183. Specifically, 200 mcl of the test mixture were transferred to a well of a polystyrene plate coated with polyclonal rabbit anti-HIV p24. Following overnight antigen capture at room temperature, the plates were washed with phosphate buffered saline containing Tween-20 (PBST). Detection of the antibody-antigen complex was accomplished with biotinylated rabbit anti-p24 in a 2 hour incubation at 37° C. Following washes with PBST, the antibody-antigen-antibody-biotin complex was further complexed with streptavidin-horseradish peroxidase for 15 minutes at room temperature, which thereafter was reacted with an o-phenylalanine diamine (OPD) substrate producing a colored product. Absorbance of the product was measured at 490 nm using a spectrophotometer (Bio-Tek Instruments). A standard curve (range 31 to 1000 ng/l) was established utilizing a whole virus lysate whose p24 protein concentration was compared with affinity-purified p24 antigen. The protein concentration of this purified antigen was measured by the Burnett method. Standard curve and sample performance was evaluated by quadrantic analysis utilizing a statistical package provided by Du Pont. Qualitative controls for each assay included serum samples containing viral lysate equivalent to 15 ng/l p24 protein. The reproducible lower limit of antigen detection was less than 31 ng/l yet greater than 15 ng/l. Quantitative values less than 31 ng/l were considered to be 30 ng/l for statistical analysis.

p24 antigen concentrations for the antigen solution were determined for each assay using the same p24 assay protocol. Controls consisted of aliquots of sera with varying titers of p24 binding capacity which were included with each assay. The nonspecific binding of serum for p24 was established among subjects at no risk for HIV infection.

The binding capacity (p24 BC) of a sample in ng/ml was calculated from the following formula, where A is the p24 antigen concentration in ng/ml of the antigen solution, B is the final p24 antigen concentration in ng/ml of the test mixture, V is the volume of the test mixture (mcl), and Q is the volume of the undiluted serum sample (mcl):

$$p24\ BC = [A-B] \times [V/Q].$$

As discussed above, one particularly important advantage of the anti-p24 antibody assay of the present invention is the ease with which it can be integrated with a p24 antigen assay. Thus, for the protocol described above, both an anti-p24 antibody assay and a p24 antigen assay can be performed on a patient's serum by simplying taking one or a few extra samples of serum, mixing them with the antigen solution, incubating them at 37° C., and then running a standard p24 antigen assay for these extra samples along with the samples one would normally run to determine the patient's level of p24 antigen. Plainly, these few added steps are easy to teach to clinical laboratory personnel already familiar with the p24 antigen assay.

Without intending to limit it in any manner, the present invention will be more fully described by the following examples.

EXAMPLES

I. Summary of Results

Two hundred fourteen untreated subjects were followed (range 12-42 months) to study the natural history of HIV infection: 110 were classified as CDC II/III, 11 as CDC IV A, 15 as CDC IV D, 31 as CDC IV C, and 47 were HIV-seronegative controls. p24 binding capacity and quantitative levels of HIV p24 antigen in serum were determined at regular intervals. For people in all diagnostic groups, a p24 BC below 31 ng/ml was more closely associated with progressive disease than was p24 antigen positivity: 87% of CDC IV C, 89% of CDC IV A, 69% of CDC IV D, and 21% of CDC II/III subjects had p24 BC less than 31 ng/ml at entry, while 65% of CDC IV C, 64% of CDC IV A, 60% of CDC IV D, and 13% of CDC II/III subjects were p24 antigenemic. Prospective analysis of 47 CDC II/III men followed for 3 years who showed actuarial progression rates to ARC at 4%, 13%, and 23% and to AIDS at 5%, 8%, and 8% at 1, 2, and 3 years, indicated that levels of p24 BC below 31 ng/ml were more strongly associated with progression than was p24 antigenemia ($X^2$32 20.6 versus 4.6). Overall, it was concluded that quantitative measures of p24 binding capacity and p24 antigen were powerful indicators of progressive disease.

II. Methods

A. Patient Population

Two hundred and fourteen (n=214) subjects were recruited between Jan. 1984 and Mar. 1987. These included 110 asymptomatic HIV-seropositive and 47 seronegative people, 11 patients with AIDS-related complex (ARC, Centers for Disease Control ("CDC") classification CDC IV A), 15 with Kaposi's sarcoma (KS, CDC IV D), and 31 with the opportunistic infection, *Pneumocytis carinii* pneumonia (AIDS/OI, CDC IV CI). Study participants were seen at six month intervals or more frequently when clinical symptoms were reported. All subjects gave informed consent for HIV virus testing in accordance with the guidelines of the U.S. Public Health Service. Initial serological evaluation was performed by one of several ELISAs (Abbott, Du Pont, or Cellular Products, Inc.) with confirmation by Western blotting of serum (Biotech Research Laboratories, E. I. Du Pont, Bethesda, Md.).

B. Assays p24 BC values were determined using the assay protocol described above. p24 antigen concentrations were determined using the Du Pont assay described above.

Levels of anti-p24 were also measured on selected samples by an experimental enzyme immunoassay utilizing a recombinant gag gene product expressed in *E. coli* (E. I. Du Pont, Glascow, Del.). Serial dilutions of serum samples (1:20 to 1:43740 in three-fold steps) were incubated in 200 microliter volumes with recombinant HIV p24 fixed in wells of a polystyrene microtiter plate for 1 hour at 37° C. Following washing with PBST, the wells were incubated with alkaline phosphatase conjugated anti-human globulin for 30 minutes at 37° C. Following further washes, para-nitrophenylphosphate (pNPP) substrate was added to the wells and incubated for 30 minutes at 37° C. The reaction was stopped by the addition of 50 microliters of 3N NaOH and the absorbance of the solution was read at 405 nm by a spectrophotometer. Positive results were defined as a sample absorbance twice the mean of negative control values. The reciprocal of the maximum serum dilution to be scored positive was taken as the measure of the antibody in the sample.

Complete blood counts (Coulter Electronics, Hialeah, Fla.) with white cell counts (WBC) and lymphocyte subset profiles were obtained at 6 month intervals for the asymptomatic seropositive men and seronegative controls. Study subjects in advancing stages of infection underwent complete blood counts and lymphocyte subset profile analysis at varying intervals, depending upon clinical status. Lymphocyte subsets were quantitated utilizing monoclonal antibodies Leu 4, Leu 3a, and Leu 2a (Becton Dickinson, Sunnyvale, Calif.) which label the lymphocyte receptors CD3, CD4, and CD8 respectively, and by FACS (fluorescein-activated cell sorting).

C. Statistical Analysis

Analysis of data was initially performed with the patients grouped by admitting diagnosis. The variables associated with outcome were established by discriminant analysis. The data were also analyzed with samples grouped by diagnosis, outcome, and visit number. Group differences were compared by one-way ANOVA with Fisher's least significance test. Grouped data were also analyzed by nonparametric methods, particularly the Mann-Whitney two sample test and the Kruskal-Wallis test of multiple group samples. Relationships among variables were established by correlation analysis and chi squares. Prospective data were analyzed by the product-limit method and the differences among the actuarial progression rates were evaluated by ANOVA. See Cox, et al., *Analysis of Survival Data*, Chapman and Hall, London, 1984. Statistical significance implies a p value of less than or equal to 0.05 unless stated otherwise.

III. Results

A. Analysis of entry data with patients grouped by diagnosis

Table 1 shows selected entry laboratory values by diagnostic category. All HIV-infected groups showed significant reduction in total numbers of white blood cells (WBC) and CD4+ lymphocytes (helper cells) from levels in seronegative controls. Patients with ARC or AIDS/OI had significantly decreased numbers of WBC and CD4+ cells compared to subjects classified as CDC II/III, while KS patients had levels intermediate between asymptomatic men and ARC/AIDS patients. Although there was overlap of the 95% confidence level ranges, both asymptomatic subjects and patients with Kaposi's sarcoma had somewhat higher numbers of CD8+ lymphocytes than other patients (n.s., p=0.08) or controls.

While HIV p24 antigen was detected at entry in subjects from all groups, the frequency of positive samples and the quantitative level of antigen (range 30–832 ng/l) was greater in symptomatic patients than in asymptomatic subjects ($X^2=61.6$, p less than 0.001). Of 31 patients with a history of opportunistic infection, 20 (65%) were p24 antigenemic at entry (range 31–832 ng/l). Sixty-four percent (7/11) of ARC patients were antigenemic at entry (range 30–623 ng/l); and for the 15 patients presenting with KS, 60% were p24 positive at entry (range 30–204 ng/l). Asymptomatic subjects were less frequently p24 positive at entry (14/110, 13%, range 30–240). If persistent antigenemia was defined as two or more p24-positive samples collected at least 4 weeks apart, 12/15 AIDS patients, 3/5 ARC patients, and 8/47 asymptomatic subjects were found to be persistently antigenemic.

The level of p24 BC of serum varied among the diagnostic groups (range 0–114 ng/ml): the background p24 BC among seronegative controls (n=47) at no risk for occult HIV infection was 9±1 ng/ml. p24 BC levels were highest among asymptomatic subjects (mean 50±2, range 6–114 ng/ml). Patients with KS showed lower mean levels at entry (33±4, p 0.05) than asymptomatic subjects. Patients with ARC or AIDS/OI had still lower levels of p24 BC (mean 14±3, 13±3 respectively, p=0.01). When the quantitative level of p24 BC was dichotomized above or below 31 ng/ml (a break point which discriminated between asymptomatic and symptomatic subjects, $X^2=39.2$, p less than 0.001), 19/89 (21%) asymptomatic subjects showed less than 31 ng/ml of p24 BC at entry. Among symptomatic patients, 9/13 (69%) patients with KS, 8/9 (89%) of patients with ARC, and 13/15 (87%) of patients with AIDS/OI had p24 BC less than 31 ng/ml at entry.

B. Prospective analysis of laboratory data from all diagnostic groups

For all patient groups, p24 antigenemia greater than or equal to 31 ng/l was strongly associated with progression ($X^2=11.2$, p less than 0.001). While the difference in level of association was small, an entry level p24 BC less than 31 ng/ml was somewhat better associated with progressive disease than p24 antigen positivity at entry ($X^2=41.3$ and 6.8, respectively). When levels of CD4+ lymphocytes were dichotomized below or above 400 cells/mm³, both entry p24 antigenemia and levels of p24 BC less than 31 ng/ml were more closely associated with symptoms than numbers of CD4+ cells ($X^2=61.6$, 39.2, and 17.9).

Among the HIV-seronegative high-risk control group, 2 subjects were noted with outlying values for p24 BC (greater than 3 standard deviations above mean for low-HIV-risk seronegative individuals, 9±1). One man, a 31 year old homosexual with a history of high risk sexual activity with a rising p24 BC (initially 5 ng/ml followed 6 months later by 18 ng/ml), has been culture and serum antigen negative on several occasions but has HIV DNA in uncultured lymphocytes by enzymatic amplification and oligomer cleavage detection (polymerase chain reaction (PCR)). See Kwok et al., "Identification of human immunodeficiency virus sequences by using in vitro enzymatic amplification and oligomer cleavage detection", *J. Virol.*, 1987, Vol. 61, pages 1690–94. The second man, a 43 year old homosexual reporting occasional high risk sexual activity, has also shown an elevated level of p24 BC (25 ng/ml). This subject has had several weakly positive HIV serologies by indirect immunofluorescence followed by negative serologies by the same technique. Although cultures and seru antigen levels have been consistently negative, occult infection remains to be excluded.

C. Prospective analysis of asymptomatic subjects

Figure 1:
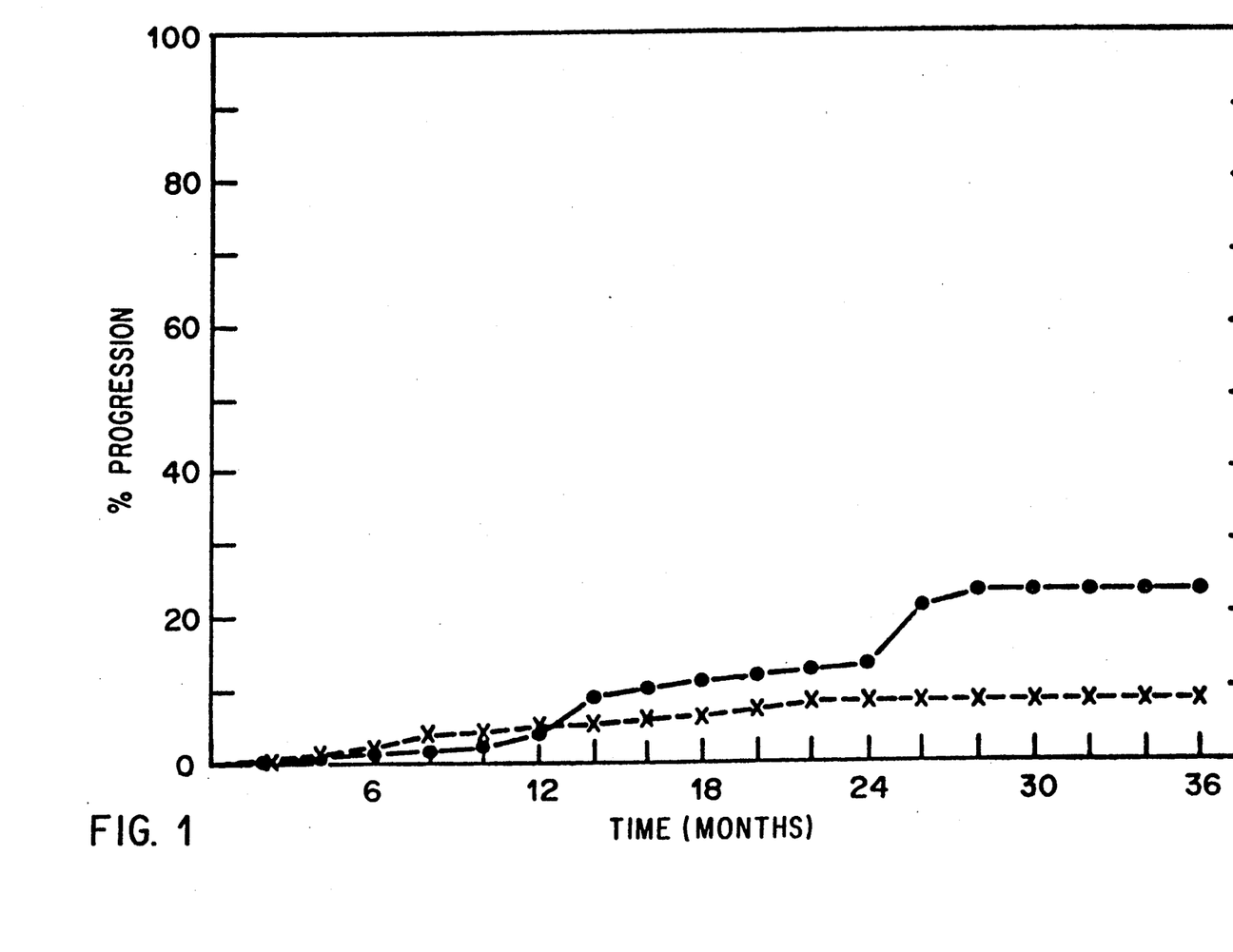
FIG. 1 shows actuarial progression rates to ARC or AIDS in 47 subjects asymptomatic at entry.
Figure 2A:
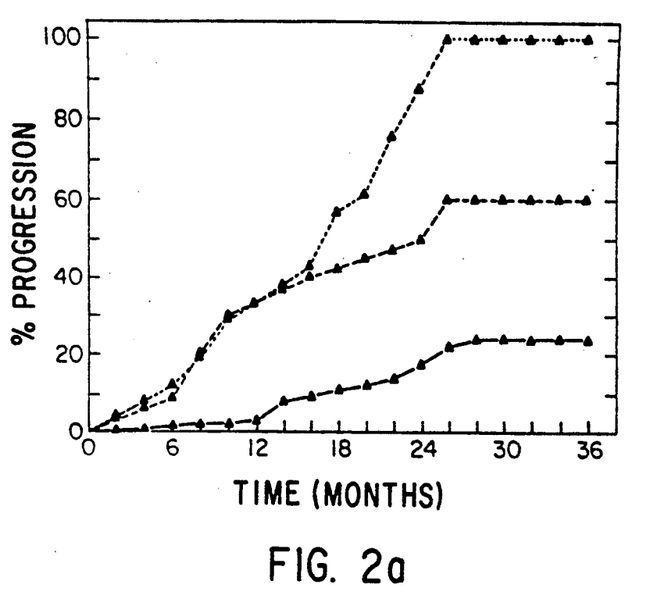
FIG. 2a shows actuarial progression rates to ARC and AIDS by levels of p24 antigenemia: solid triangle/solid line—p24 negative at entry: solid triangle/dashed line—p24 positive at entry: solid triangle/dotted line—p24 greater than 31 ng/l at entry.
Figure 2B:
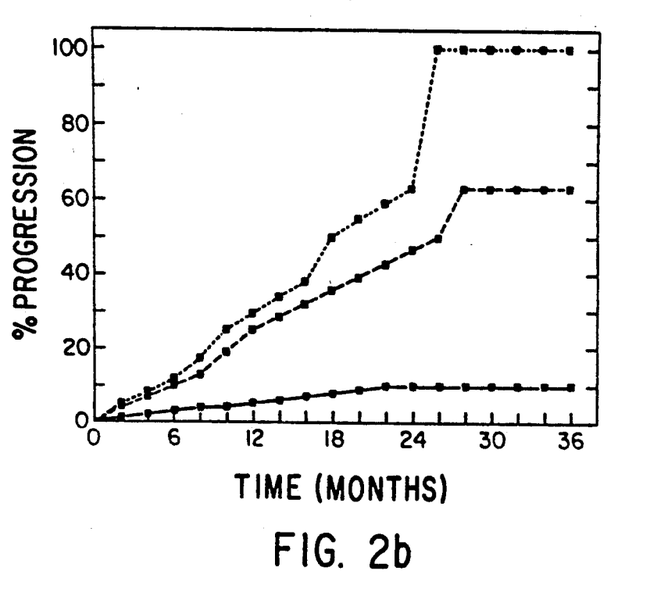
FIG. 2b shows actuarial progression rates to ARC and AIDS by levels of p24 binding capacity: solid square/solid line—p24 BC equal to or greater than 47 ng/ml; solid square/dashed line—p24 BC 31-47 ng/ml: solid square/dotted line—p24 BC less than 31 ng/ml.
Figure 2C:
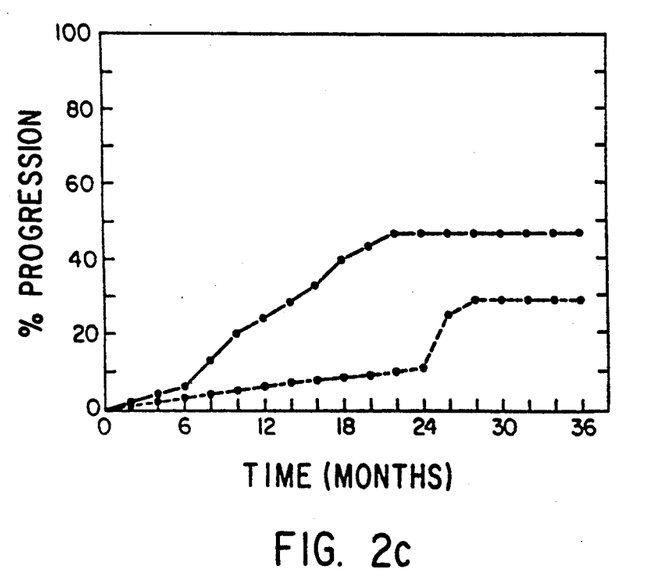
FIG. 2c shows actuarial progression rates to ARC and AIDS by levels of CD4+ lymphocytes (helper cells): solid circle/dashed line—CD4+ cells greater than 400 cells/mm³; solid circle/solid line—CD4+ cells less than 400 cells/mm³.
Figure 2D:
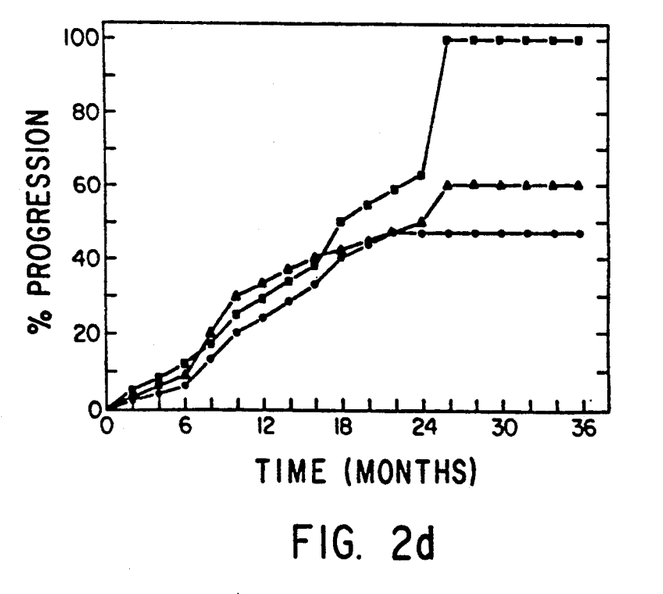
FIG. 2d shows actuarial progression rates to ARC and AIDS by p24 antigenemia, p24 BC, and CD4+ cells: solid triangle—p24 antigen positive at entry: solid square—p24 BC less than 31 ng/ml; solid circle—CD4+ cells less than 400 cells/mm³.

A cohort of asymptomatic seropositive homosexual men (n=47) who were seen on at least 3 occasions during the 3 year study period and who were not treated with antiviral agents were studied to evaluate the use of several laboratory markers to establish prognosis. The actuarial progression rate to ARC was 4%, 13%, and 23% at 1, 2, and 3 years respectively: the actuarial progression rate to AIDS was 5%, 8% and 8% at 1, 2, and 3 years respectively (FIG. 1). Groups for analysis were established by outcome.

Figure 4A:
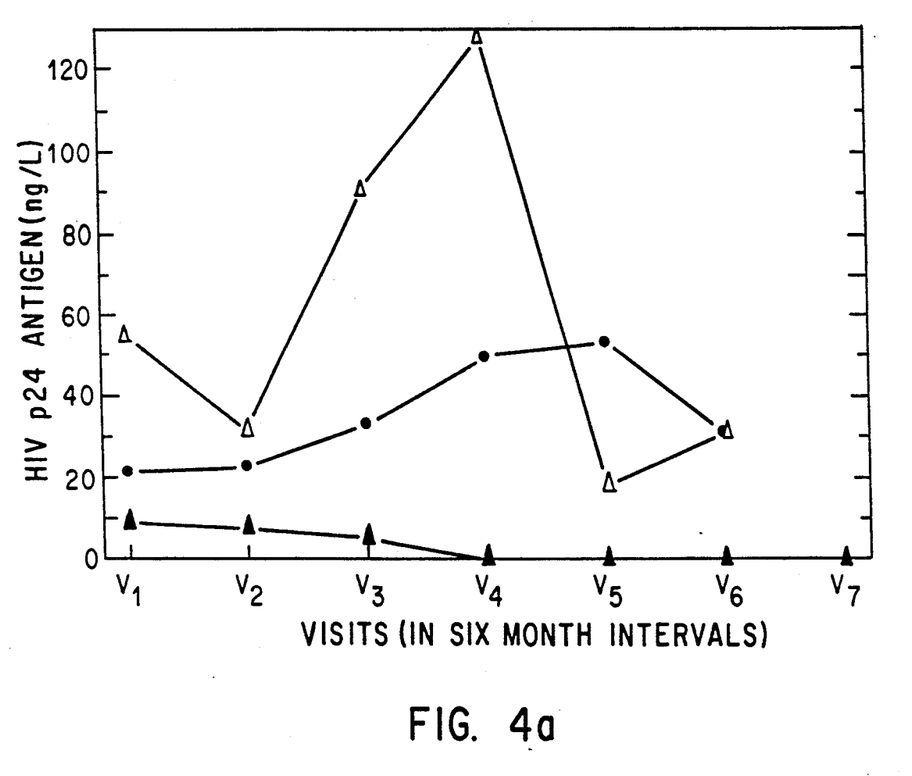
FIG. 4a shows levels of HIV p24 antigen (ng/l) in serum of men asymptomatic at entry and grouped by current diagnosis. Visits are at six month intervals. Outcomes are noted as follows: solid triangles—CDC II-/III; solid circles—CDC IV A: open triangles—CDC IV C.
Figure 4B:
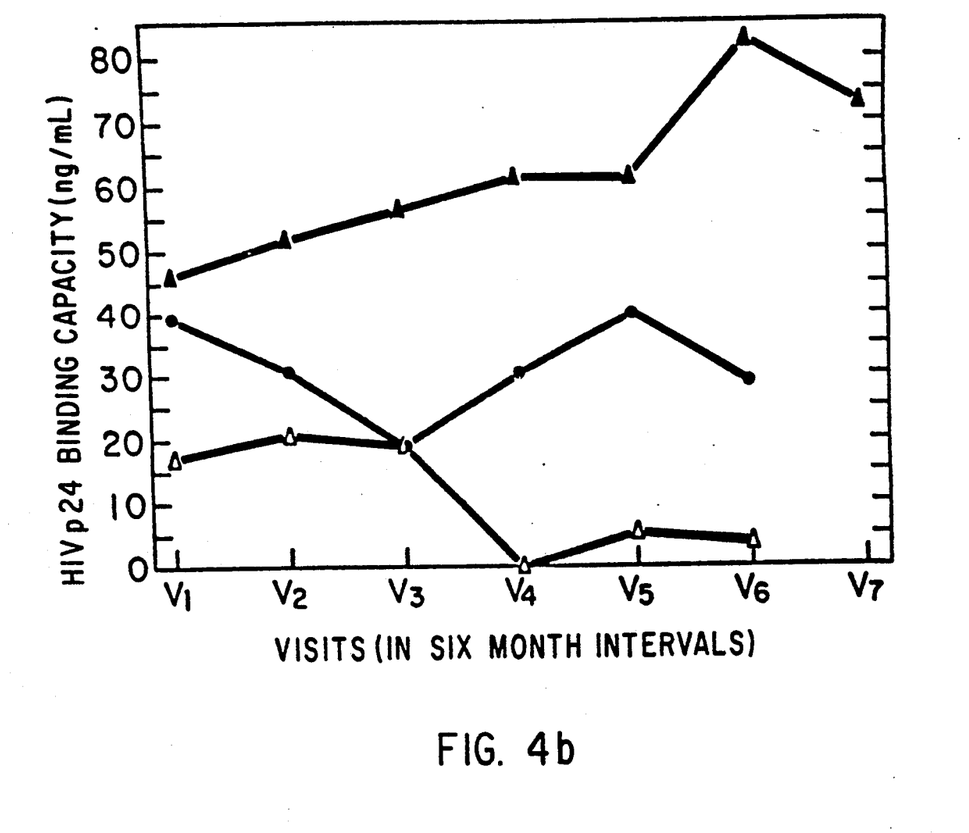
FIG. 4b shows levels of HIV p24 binding capacity (p24 BC, ng/ml) of serum of men asymptomatic at entry and grouped by current diagnosis. Visits are at six month intervals. Outcomes are noted as follows: solid triangles—CDC II/III; solid circles—CDC IV A; open triangles—CDC IV C.

At entry, there were no significant differences in the mean numbers of WBC, CD4+ or CD8+ lymphocytes among the outcome groups. Subjects who progressed to AIDS had lower entry levels of CD4+ cells (not significant), with marked variation in the number of cells among these subjects. There was a significant difference in the mean entry level of p24 antigen and p24 BC between those progressing to AIDS and the stable subjects or those progressing to ARC (FIGS. 4a and 4b, p=0.01). Levels of p24 BC below 31 ng/ml at entry were strongly associated with progression ($X^2=20.6$, p less than 0.001); levels of p24 BC between 31–47 ng/ml were also associated with progression ($X^2=7.8$, p less than 0.01) (Table 2). p24 antigenemia at any quantitative level was significantly associated with progression ($X^2=4.6$, p less than 0.05), although not as strongly as p24 BC. If p24 antigenemia was defined as p24 greater than or equal to 31 ng/l, the association of p24 antigenemia with progression became stronger ($X^2=14.3$, p less than 0.001). Taken independently, p24 antigen positivity with quantitative levels less than 31 ng/l did not correlate with progression. The combination of p24 antigenemia and p24 BC less than 31 ng/ml at entry was a powerful predictor of progression ($X^2=25.2$). Using dichotomized entry laboratory values, numbers of CD4+ lymphocytes above and below 400 cells/mm³ failed to predict progression ($X^2=1.42$). Levels of anti-p24 antibody as measured by the recombinant gag assay did not correlate with outcome for the group.

Product-moment analysis of the relationship between the levels of the variables and progression are shown in FIG. 2. Subjects antigen-negative at entry were less likely to develop progressive disease than subjects antigen-positive at entry (FIG. 2a, p less than 0.001). The difference in the rates of progression based upon the stratification of subjects by the quantitative level of p24 antigen in serum was nonsignificant. The difference between the progression rates for subjects with p24 BC greater than 47 ng/ml and subjects with p24 BC 31–47 ng/ml was significant at the p=0.03 level (FIG. 2b), while the difference in progression rates for subjects with levels of p24 BC at and above 47 ng/ml or less than 31 ng/ml was significant at the p=0.0001 level. Progression rates for the levels of CD4+ cells were different (FIG. 2c), although entry levels (greater than or less than 400 cells/mm$^3$) did not significantly correlate with outcome. When the progression rates were compared (FIG. 2d), p24 BC identified the progressors most effectively, significantly more effectively than numbers of CD4+ cells at entry (p=0.05).

Figure 3A:
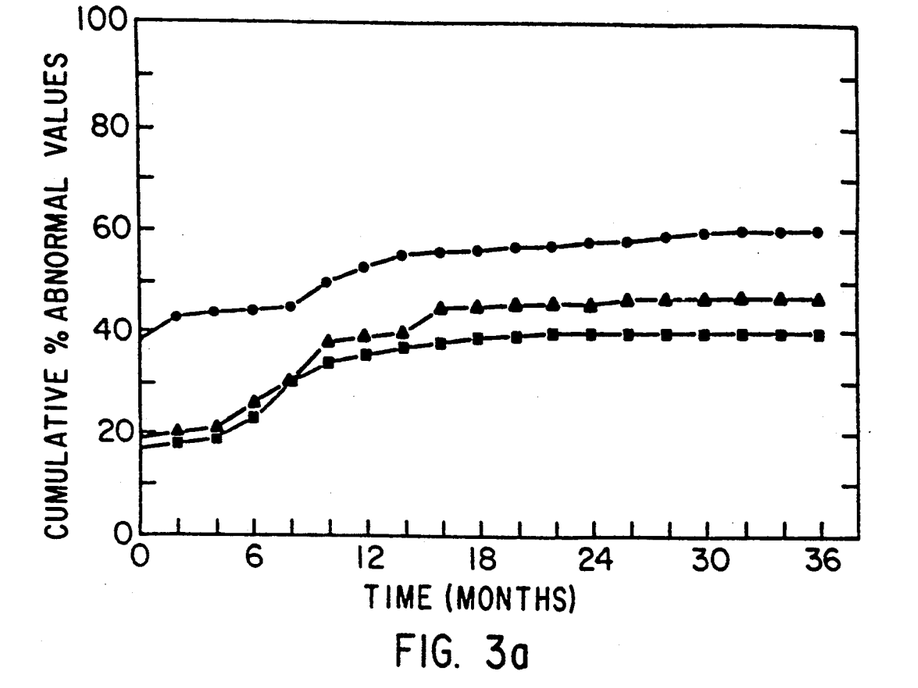
FIG. 3a shows actuarial progression rates for the appearance of abnormal laboratory values for asymptomatic subjects who did not progress: solid triangle—p24 positivity: solid square—p24 BC less than 31 ng/ml; solid circle—CD4+ cells less than 400 cells/mm³.
Figure 3B:
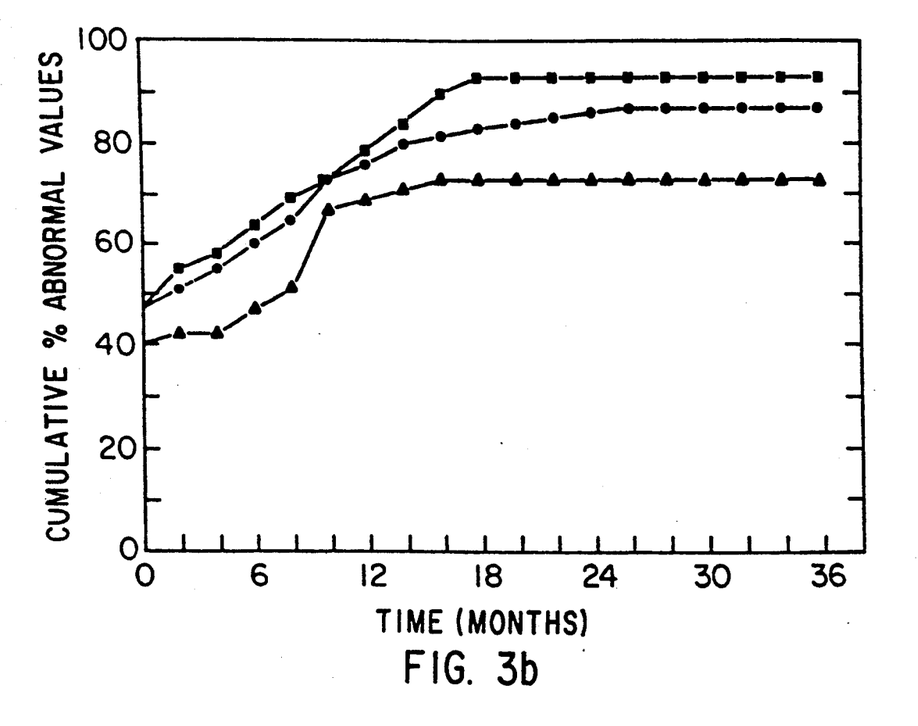
FIG. 3b shows actuarial progression rates for the appearance of abnormal laboratory values for asymptomatic subjects who progressed to ARC/AIDS: solid triangle—p24 positivity; solid square—p24 BC less than 31 ng/ml; solid circle—CD4+ cells less than 400 cells/mm³.

The actuarial rate of the appearance of index laboratory values, i.e., p24 positivity, p24 BC less than 31 ng/ml, or CD4+ cells under 400 cells/mm$^3$, was markedly different between progressors (FIG. 3a) and nonprogressors (FIG. 3b). For progressors, there was no significant difference in the rates of appearance of index values. For nonprogressors, p24 antigen-positivity was seen more frequently than abnormal levels of p24 BC (p less than 0.001), suggesting that p24 BC greater than 31 ng/ml at entry was a more reliable indicator of a stable course than the absence of p24 antigen.

Figure 4C:
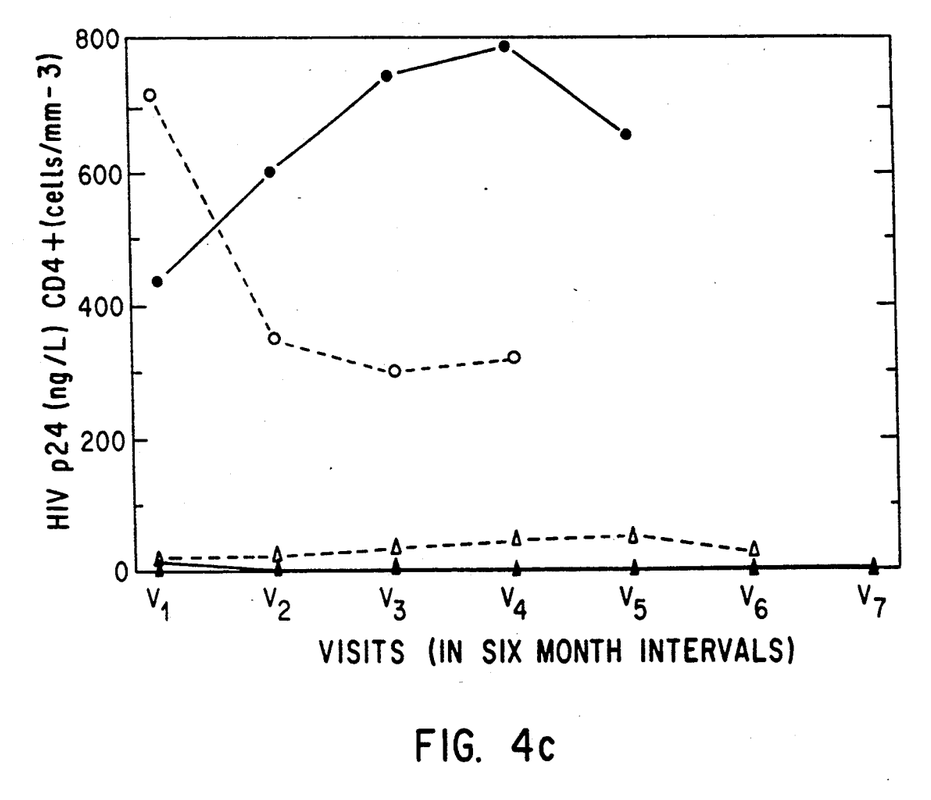
FIG. 4c shows levels of HIV p24 antigen (ng/l) (triangles) and numbers of CD4+ lymphocytes (circles) in two groups of patients: solid triangles/solid circles—CDC II/III who remained CDC II/III; open triangles/open circles—CDC II/III who progressed to CDC IV A.
Figure 4D:
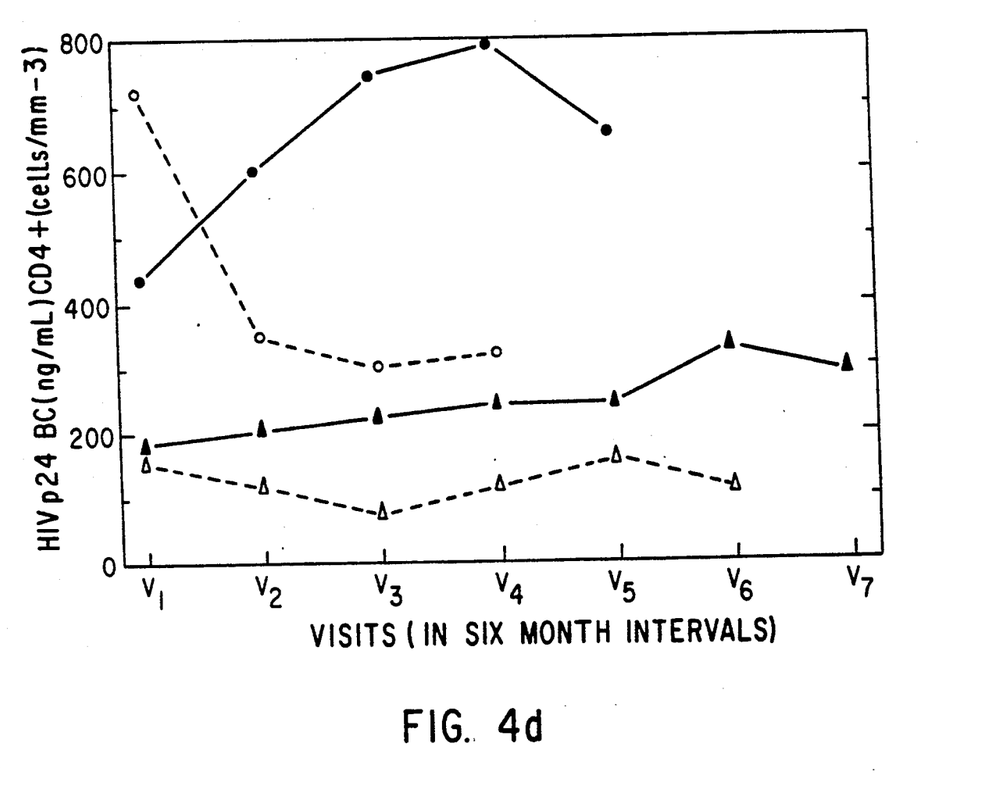
FIG. 4d shows levels of HIV p24 BC (ng/ml) (triangles) and numbers of CD4+ lymphocytes (circles) in two groups of patients: solid triangles/solid circles—CDC II/III who remained CDC II/III; open triangles/open circles—CDC II/III who progressed to CDC IV A.
Figure 5:
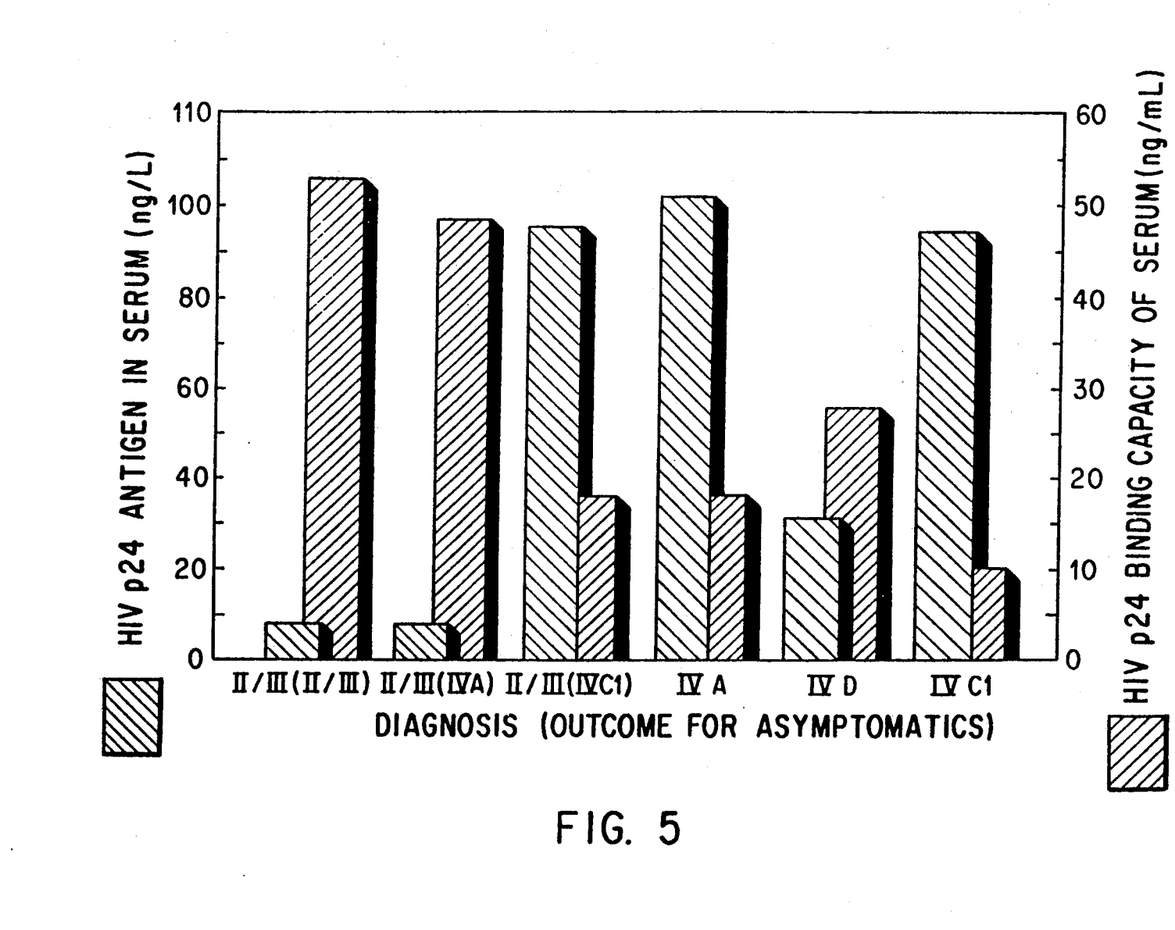
FIG. 5 shows levels of HIV p24 antigen (ng/l) and HIV p24 binding capacity (p24 BC, ng/ml) for all samples grouped by entry diagnosis (with outcome diagnosis for those initially CDC II/III).

Mean levels of p24 antigen and p24 BC during the course of observation are shown in FIGS. 4a and 4b. Detectable antigen fluctuated sharply among progressors, while levels of p24 BC showed gradual change. Among subjects who remained stable, low or falling levels of p24 antigen correlated with increasing numbers of CD4+ lymphocytes, while increasing levels of p24 antigen correlated with decreasing numbers of CD4+ cells (FIG. 4c). The presence of p24 antigen in serum was also associated with increased numbers of CD8+ lymphocytes (r=0.702, p=0.02). Levels of p24 and p24 BC in all groups showed an overall decline as patients progressed (FIG. 5).

IV. Discussion

As shown by the above results, p24 antigen level is a meaningful parameter with which to monitor HIV-infected patients. In this study, the percent of subjects with detectable p24 antigen in serum ranged from a low of 13% in asymptomatic men to a high of 65% in patients with AIDS/OI (Table 1). Not all HIV-infected subjects were antigenemic during observation; 21 of 57 (37%) symptomatic patients (CDC IV+) were p24 negative, while 96 of 110 (87%) HIV-seropositive asymptomatic subjects were p24 antigen negative.

Prospective analysis of the data revealed that the quantity and the persistence of detectable antigen were related to outcome. Only three of thirty-two asymptomatic subjects who remained stable over a three-year period had p24 antigen-positive samples with a quantitative p24 level of greater than or equal to 31 ng/l in the first year, while ten of fifteen who were initially asymptomatic but progressed in 3 years had p24 antigen levels greater than or equal to 31 ng/l during the first year ($X^2$=18.4, p less than 0.001). If persistent antigenemia was defined as two or more p24-positive samples drawn at intervals of 4 weeks or more, then persistent antigenemia was also strongly associated with progression ($X^2$=20.6, p less than 0.001). While persistent antigenemia was an indicator of poor prognosis regardless of the clinical symptoms of the patient, the absence of p24 antigenemia did not necessarily mean that the patient was going to become or remain stable. Five of 11 asymptomatic men progressing to ARC showed no detectable antigen on at least 2 visits before clinical advancement. In 2 of 4 men progressing to AIDS from the asymptomatic stage, levels of p24 antigen were negative in the 6-month period preceding diagnosis. As the levels of p24 antigen varied widely in any individual over time, it was essential that several values were obtained before an overall assessment was made.

As the above results also show, p24 BC is a further meaningful parameter with which to monitor HIV-infected patients. Cross-sectional analysis of the data showed that the levels of p24 BC generally provided mirror images of the levels of p24 antigenemia (FIG. 5). Prospective analysis illustrated the usefulness of the determination of p24 BC. Among asymptomatic subjects who progressed to ARC/AIDS, a p24 BC less than 31 ng/ml (abnormal for the asymptomatic group) was found more frequently at entry (n.s.) and significantly more frequently by 18 months of follow-up than p24 antigenemia (FIG. 3a, p less than 0.001). Among nonprogressors from the same group, an abnormal p24 BC was seen less frequently than p24 antigenemia both at entry and throughout the 3 year period (FIG. 3b, p less than 0.001). For asymptomatic subjects developing ARC, 5 of 11 subjects were p24 antigen negative during the year prior to progression, while all 11 of these men had intermediate to low levels of p24 BC (FIGS. 4a and 4b).

It should be noted that the anti-p24 antibody assay of the present invention does not directly measure antibody to p24, but instead measures the ability of a sample to complex known amounts of antigen. Levels of anti-p24 as measured by the recombinant p24 ELISA used in this study did not correlate with levels of p24 BC. This may, in part, be due to the small number of samples for which both assay techniques were used. Also, although not wishing to be bound by any particularly theory or theories of operation, it is believed that the in vitro immune complex formation which occurs in the p24 BC assay may favor measurement of high affinity antibodies, while the recombinant ELISA may detect antibodies of lower affinity. Because of these theoretical considerations, the term "p24 binding capacity" has been used herein to describe the observed data rather than the term "antibody level". In addition, it is considered possible that high affinity antibodies may disappear prior to the loss of low affinity antibody.

Although not wishing to be bound by any particular theory or theories of operation, it is believed that a reduction in p24 BC levels probably reflects binding of p24 antibody into antigen-antibody complexes, the antigen being the result of chronic viral proliferation. See Ujhelyi et al., "A simple method for detecting HIV antibody hidden in circulating immune complexes", *AIDS*, 1987, Vol. 1, pages 161-165. An excess of antibody to antigen, particularly during the asymptomatic stage of infection, could produce a situation in which antigen is undetectable while levels of p24 BC might show measurable decline during low-grade viral proliferation. It is believed that this probably accounts for the earlier decline in p24 BC levels than the appearance of p24 antigen in asymptomatic men. Yet in some groups of patients with advanced disease, the levels of p24 BC seem disproportionately low compared to levels of detectable antigen. Stacked bar graphs of the detectable p24 antigen and p24 BC by diagnostic groups show that patients with advanced disease had somewhat less p24 BC than would be expected by comparison to other diagnostic groups (FIG. 5). The general debilitation of the immune system may be responsible for this finding.

In sum, the foregoing data demonstrates that: 1) the presence of p24 antigenemia, particularly with a quantitative level of greater than 31 ng/l or with persistence of antigenemia, is an useful indicator of progressive disease, and 2) quantitative measurement of p24 BC is more strongly associated with prognosis than is antigenemia. The results regarding p24 BC are in contrast with those of Moss et al., "Seropositivity for HIV and the development of AIDS or AIDS related condition: three year follow up of the San Francisco General Hospital cohort", Br. Med. J., 1988, Vol. 296, pages 745-750. Moss et al., however, used the technique of visual inspection of Western blots for estimation of anti-p24. This technique is imprecise and does not always correlate with measurement of p24 BC (data not shown). It is believed that these factors probably account for the difference between the above data and the Moss et al. report.

The identification of a useful anti-retroviral agent, zidovudine, has encouraged both the medical community and the HIV-infected patient population to invest time, energy, and resources toward further treatment refinements. See Yarchoan et al., "Development of antiretroviral therapy for the acquired immunodeficiency syndrome and related disorders: a progress report", New England J. Med., 1987, Vol. 316, page 258. Pretreatment patient stratification is critical for successful comparison of therapeutic regimens; regimens that might treat not only the end-stage of HIV infection, AIDS, but also the earlier stages of asymptomatic infection. Measures of virus activity will play an increasingly important role in the initial stratification and follow-up of patients undergoing therapy. The foregoing data shows that the p24 BC assay and the p24 antigen/p24 BC assay system of the present invention provide effective and convenient methods for making this stratification.

TABLE 1

CROSS-SECTIONAL LABORATORY PROFILES AT ENTRY BY DIAGNOSTIC GROUP

| Diagnosis[1] | WBC | # CD4+ | # CD8+ | p24[2] # +/# | ng/l | p24 BC[3] # < 31/# | ng/ml |
|---|---|---|---|---|---|---|---|
| Control | 6160 (486) | 803 (131) | 467 (89) | 0/50 | | 47/47 100% | 9 (1) |
| CDC II/III | 5002*+ (114) | 493* (29) | 642 (32) | 14/110 13% | 0 (0-37) | 19/89 21% | 50* (2) |
| CDC IV A | 3700*+ (424) | 162*+ (69) | 337+ (121) | 7/11 64% | 33+ (0-397) | 8/9 89% | 14+ (3) |
| CDC IV D | 4263*+ (339) | 414* (84) | 577 (88) | 9/15 60% | 30+ (0-68) | 9/13 69% | 33*+ (4) |
| CDC IV C1 | 3380*+ (816) | 170*+ (64) | 342 (152) | 20/31 65% | 31+ (0-191) | 13/15 87% | 13+ (3) |

[1]Diagnosis by Centers for Disease Control classification. For WBC, CD4+ cells, and CD8+ cells, the values reported are mean values with (standard error of the mean).
[2]For p24 antigen, the values reported are # positive patients/total # of patients with %, and median values in ng/l with (10-90% quartile range).
[3]For p24 BC, the values reported are number of patients with entry p24 BC less than 31 ng/ml over the total number of patients with entry samples with %, and the mean levels in ng/ml with (S.E.M.)
*Difference from Control, $p = 0.01$.
+ Difference from CDC II/III, $p = 0.05$.
Note:
Not all tests were performed on all subjects at each visit so that the totals do not equal 251 in all cases.

TABLE 2

INDEX LABORATORY VALUES BY YEAR FOR THE ASYMPTOMATIC SEROPOSITIVE GROUP AND PROGRESSORS

| | CDC II/III | | | CDC IV A | | | CDC IV C | | |
|---|---|---|---|---|---|---|---|---|---|
| | Year | | | | | | | | |
| | 1 | 2 | 3 | 1 | 2 | 3 | 1 | 2 | 3 |
| Actuarial progression rate | | | | 4% | 13% | 23% | 5% | 8% | |
| # progressed/ # total | | | | 2/11 | 4/11 | 5/11 | 2/4 | 2/4 | |
| Index value | | | | | | | | | |
| p24+ | 8/43 | 3/24 | 1/13 | 1/2 | 4/5 | 8/9 | 2/2 | 1/1 | N.A. |
| p24 ≧ 31 | 3/43 | 0/24 | 0/13 | 2/2 | 2/5 | 5/9 | 1/2 | 1/1 | N.A. |
| p24 BC > 48 | 30/43 | 20/23 | 10/13 | 0/2 | 1/5 | 0/9 | 0/2 | 0/1 | N.A. |
| p24 BC 31-47 | 4/43 | 2/23 | 0/13 | 2/2 | 3/5 | 0/9 | 1/2 | 0/1 | N.A. |
| p24 BC < 31 | 2/43 | 1/23 | 0/13 | 2/2 | 4/5 | 4/9 | 1/2 | 1/1 | N.A. |
| CD4+ > 400 | 20/28 | 15/23 | 3/8 | 0/2 | 0/5 | 0/3 | 0/2 | 0/1 | N.A. |
| CD4+ < 400 | 8/28 | 8/23 | 5/8 | 2/2 | 5/5 | 3/3 | 2/2 | 1/1 | N.A. |

*Index value denotes the first appearance of a laboratory value as defined with number positive over the total number of available values for the group. p24 (ng/l; p24 BC (ng/ml); CD4+ (cells/mm$^3$). Not all patients and/or samples were available for each time point, so totals do not equal 47 in all cases.

What is claimed is:

1. A method for analyzing a sample of a biological fluid with regard to the level of anti-p24 antibodies therein, comprising the steps of:
   (a) forming a mixture of: 1) the sample; and 2) an antigen solution containing free p24 antigen within a predetermined concentration range, the predetermined concentration range and the volumes of antigen solution and sample being chosen so that the initial concentration of free p24 antigen in the mixture is substantially equal to the concentration of free p24 antigen in the antigen solution;
   (b) incubating the mixture under conditions whereby anti-p24 antibodies from the sample, if any, can react with free p24 antigen to form antibody-antigen complexes;

(c) assaying the mixture to obtain a concentration value for free p24 antigen in the mixture;

(d) assaying a sample of the antigen solution to obtain a concentration value for free p24 antigen in the antigen solution; and (e) determining the difference between the concentration value obtained in step (d) and the concentration value obtained in step (c), said difference being indicative of the level of anti-p24 antibodies in the sample.

2. The method of claim 1 wherein the predetermined concentration range is from about 350 nanograms per liter to about 450 nanograms per liter.

3. The method of claim 2 wherein the mixture comprises by volume approximately 250 parts antigen solution of 1 part sample.

4. The method of claim 2 wherein the predetermined concentration range is from about 380 nanograms per liter to about 425 nanograms per liter.

5. The method of claim 4 wherein the mixture comprises by volume approximately 250 parts antigen solution to 1 part sample.

6. A method for analyzing a biological fluid with regard to the levels of p24 antigen and anti-p24 antibodies therein, comprising the steps of:

(a) forming a mixture of: 1) a first sample from the biological fluid; and 2) an antigen solution containing free p24 antigen within a predetermined concentration range, the predetermined concentration range and the volumes of antigen solution and first sample being chosen so that the initial concentration of free p24 antigen in the mixture is substantially equal to the concentration of free p24 antigen in the antigen solution;

(b) incubating the mixture under conditions whereby anti-p24 antibodies from the first sample, if any, can react with free p24 antigen to form antibody-antigen complexes;

(c) assaying the mixture to obtain a concentration value for p24 antigen in the mixture;

(d) assaying a sample of the antigen solution to obtain a concentration value for free p24 antigen in the antigen solution;

(e) determining the difference between the concentration value obtained in step (d) and the concentration value obtained in step (c), said difference being indicative of the level of anti-p24 antibodies in the biological fluid; and (f) assaying a second sample from the biological fluid for p24 antigen concentration;

the assaying of steps (c), (d), and (f) being performed substantially simultaneously.

7. The method of claim 6 wherein the predetermined concentration range is from about 350 nanograms per liter to about 450 nanograms per liter.

8. The method of claim 8 wherein the mixture comprises by volume approximately 250 parts antigen solution to 1 part first sample.

9. The method of claim 7 wherein the predetermined concentration range is from about 380 nanograms per liter to about 425 nanograms per liter.

10. The method of claim 9 wherein the mixture comprises by volume approximately 250 parts antigen solution to 1 part first sample.

* * * * *